US008831173B2

(12) United States Patent
Uehara et al.

(10) Patent No.: US 8,831,173 B2
(45) Date of Patent: Sep. 9, 2014

(54) X-RAY DIAGNOSTIC APPARATUS

(75) Inventors: Hisayuki Uehara, Otawara (JP); Reiko Hashimoto, Yaita (JP); Yoshiyasu Hayashi, Nasushiobara (JP); Kunitoshi Matsumoto, Nasushiobara (JP); Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 602 days.

(21) Appl. No.: 12/904,519

(22) Filed: Oct. 14, 2010

(65) Prior Publication Data
US 2011/0096894 A1    Apr. 28, 2011

(30) Foreign Application Priority Data
Oct. 23, 2009    (JP) .................. 2009-244544

(51) Int. Cl.
*A61B 6/02*    (2006.01)
*A61B 6/00*    (2006.01)
*A61B 6/03*    (2006.01)

(52) U.S. Cl.
CPC .............. *A61B 6/4452* (2013.01); *A61B 6/035* (2013.01)
USPC ............ 378/62; 378/98.8; 378/116; 378/190; 378/197

(58) Field of Classification Search
CPC .... A61B 6/035; A61B 6/4266; A61B 6/4452; H05G 1/58
USPC ........................ 378/62, 98.8, 116, 190, 197
See application file for complete search history.

(56) References Cited

U.S. PATENT DOCUMENTS 5,058,147 A * 10/1991 Nishikawa et al. ............. 378/38
6,196,715 B1    3/2001 Nambu et al.
(Continued)

FOREIGN PATENT DOCUMENTS

CN    101212931 A    7/2008
JP    10-179561        7/1998
(Continued)

OTHER PUBLICATIONS

Office Action issued on Apr. 6, 2012 in the corresponding Chinese Application No. 201010515600.3 (with English Translation).

(Continued)

*Primary Examiner* — Thomas R Artman
(74) *Attorney, Agent, or Firm* — Oblon, Spivak, McClelland, Maier & Neustadt, L.L.P.

(57) ABSTRACT

According to one embodiment, an X-ray diagnostic apparatus includes an X-ray tube, first detector, second detector, arm, sliding mechanism, tilting mechanism, and control unit. The X-ray tube includes an anode to generate X-rays upon receiving electrons. The first detector has the first pixel size. The second detector has the second pixel size smaller than the first pixel size. The arm pivotally supports the X-ray tube, first detector, and second detector. The sliding mechanism slidably supports the first and second detectors so as to irradiate one of the first and second detectors with the X-rays generated by the X-ray tube. The tilting mechanism tiltably supports the X-ray tube to change the size of an effective X-ray focal spot on the anode. The control unit controls the sliding of the first and second detectors by the sliding mechanism upon interlocking with the tilting of the X-ray tube by the tilting mechanism.

12 Claims, 9 Drawing Sheets

(56) References Cited

U.S. PATENT DOCUMENTS

| | | | |
|---|---|---|---|
| 6,285,739 B1 | 9/2001 | Rudin et al. | |
| 7,029,177 B2 * | 4/2006 | Watanabe et al. | 378/197 |
| 7,170,974 B2 | 1/2007 | Groh et al. | |
| 7,577,232 B2 * | 8/2009 | Tachibana et al. | 378/39 |
| 2006/0256921 A1 * | 11/2006 | Tachibana et al. | 378/116 |
| 2008/0069298 A1 * | 3/2008 | Hoffman et al. | 378/19 |
| 2009/0168966 A1 * | 7/2009 | Suzuki et al. | 378/116 |
| 2010/0142671 A1 * | 6/2010 | Gregerson et al. | 378/19 |

FOREIGN PATENT DOCUMENTS

| | | |
|---|---|---|
| JP | 2001-95790 | 4/2001 |
| JP | 2001-145617 | 5/2001 |
| JP | 2003-111754 | 4/2003 |
| JP | 2004-105568 | 4/2004 |
| JP | 2005-152640 | 6/2005 |
| JP | 2005-237524 | 9/2005 |
| JP | 2005-245814 | 9/2005 |
| JP | 2006-296898 | 11/2006 |
| JP | 2007-54528 | 3/2007 |
| JP | 2007-105345 | 4/2007 |
| JP | 2008-142236 | 6/2008 |
| JP | 2008-229270 | 10/2008 |
| WO | WO 2009/019935 A1 | 2/2009 |

OTHER PUBLICATIONS

Office Action mailed Mar. 11, 2014, in Japanese Patent Application No. 2010-198077, (w/English translation), (7 pages).

* cited by examiner

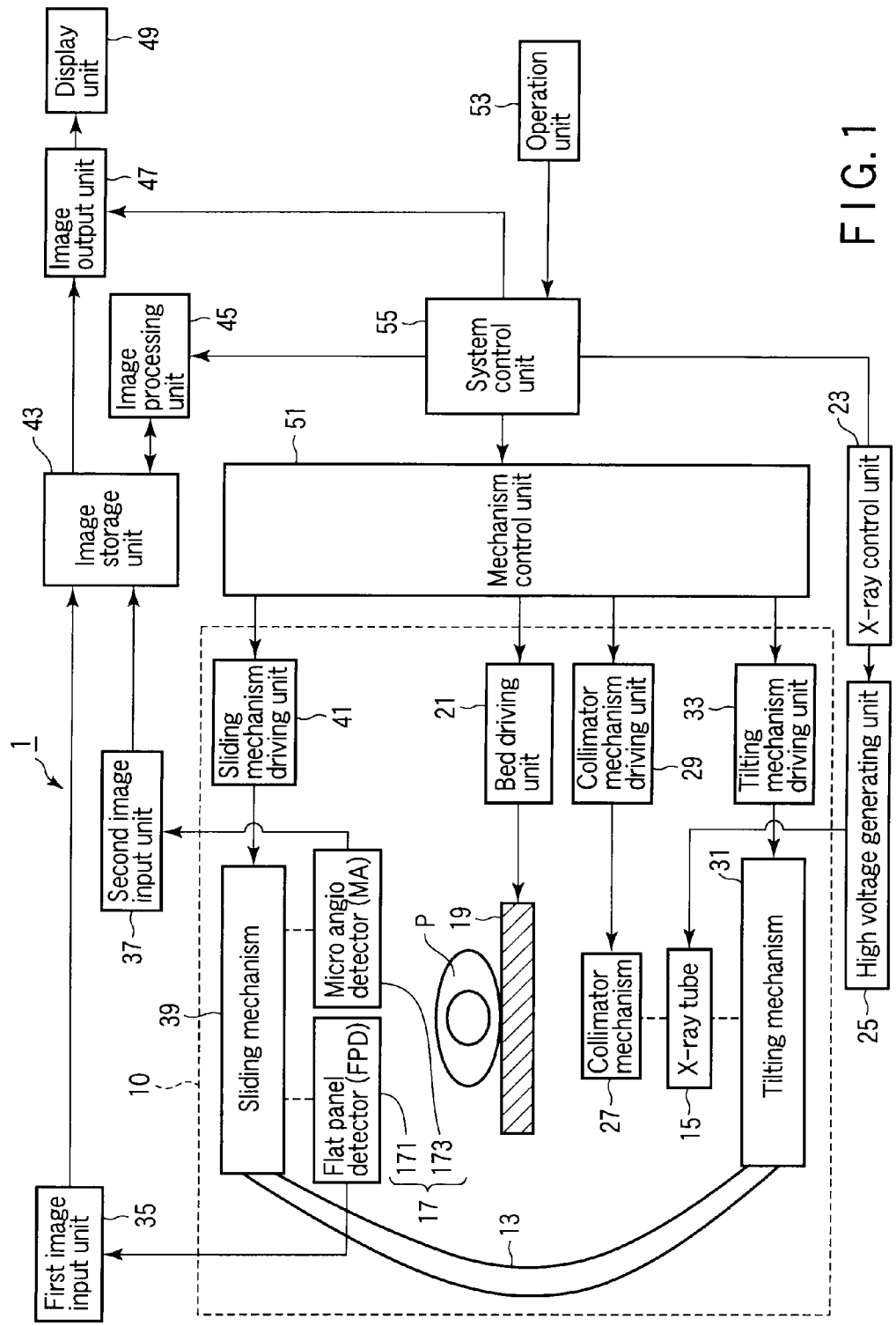
F I G. 1

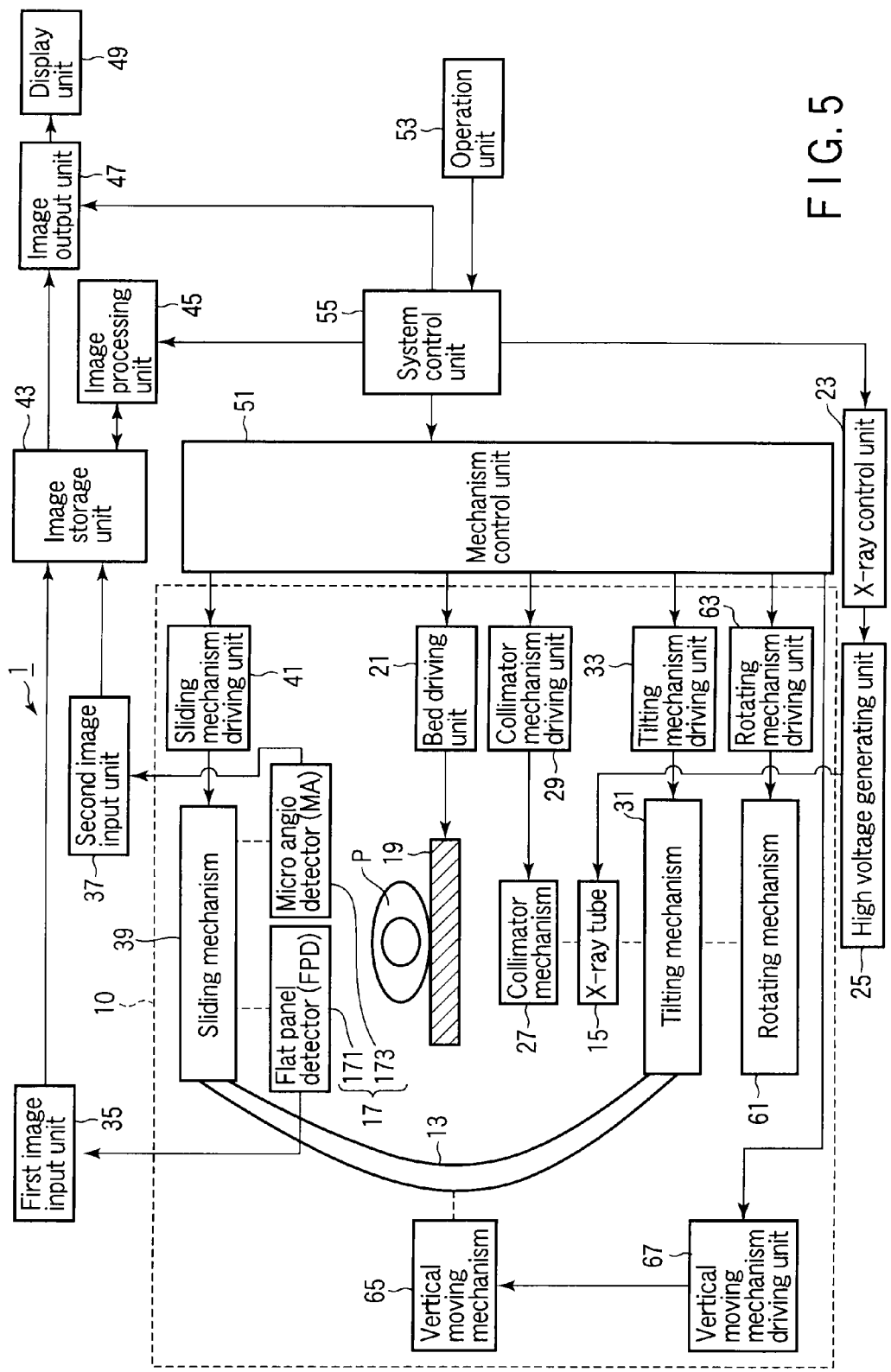
F I G. 5

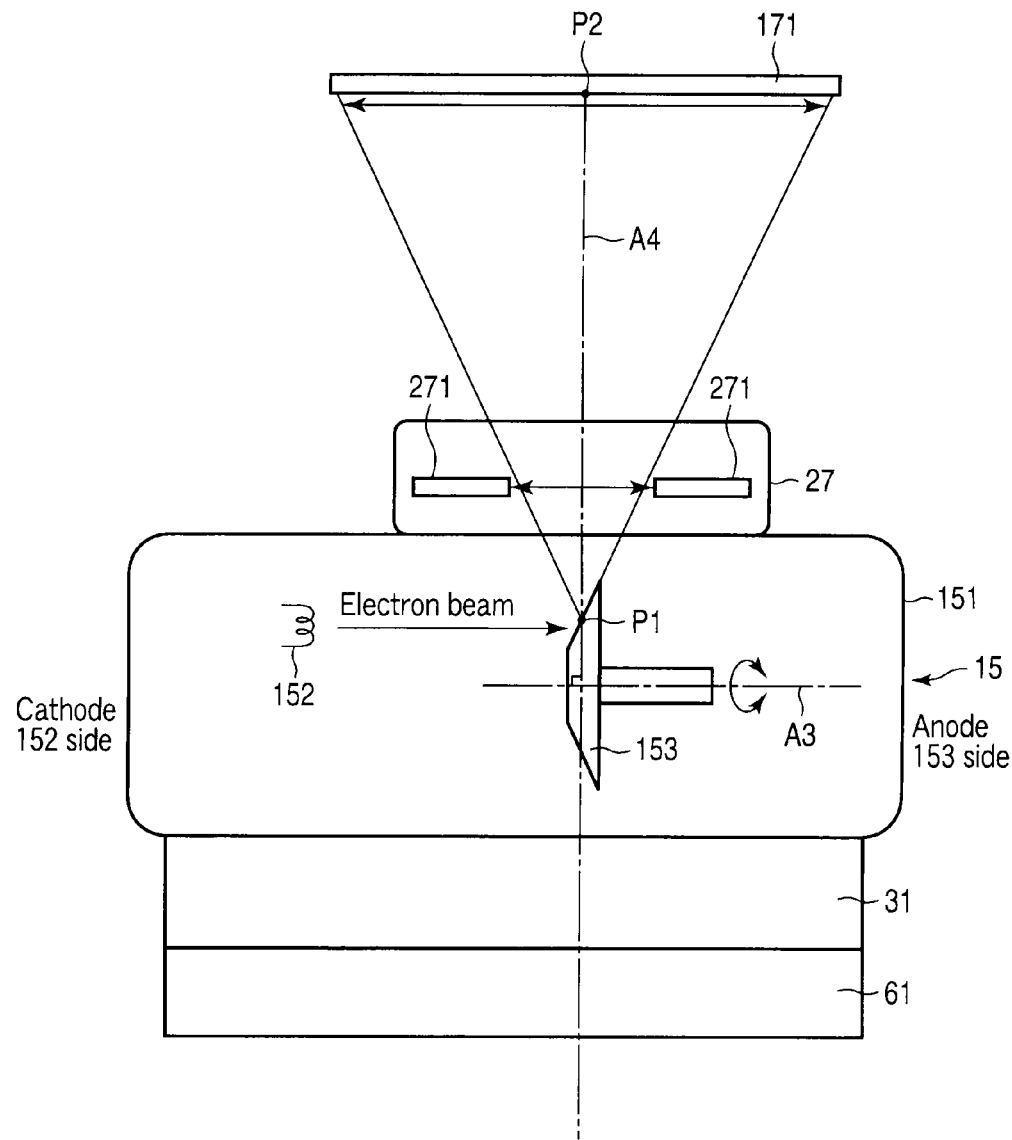
F I G. 7

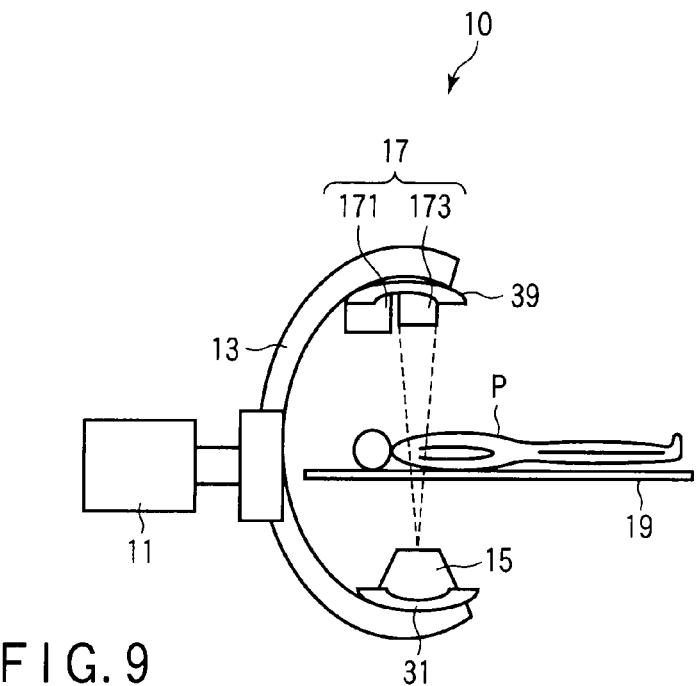
FIG. 9 At time of normal fluoroscopy/radiography
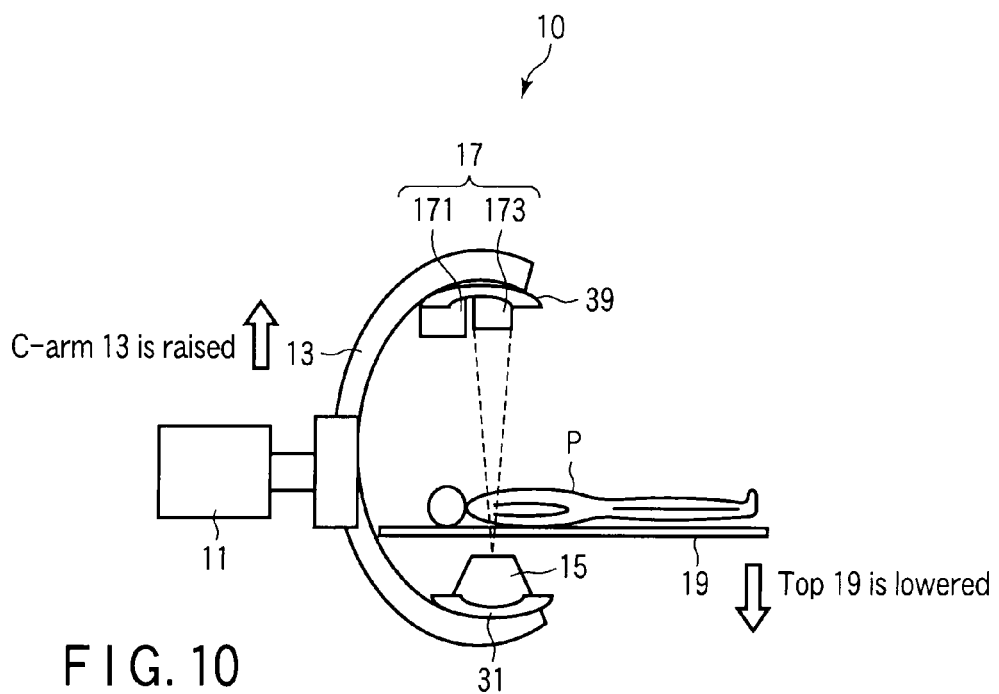
FIG. 10 At time of enlargement fluoroscopy/radiography FOV positions with detection surface being fixed
(FPD 171 and MA 173 are slid only when FOV sizes M2 and M3 are switched)
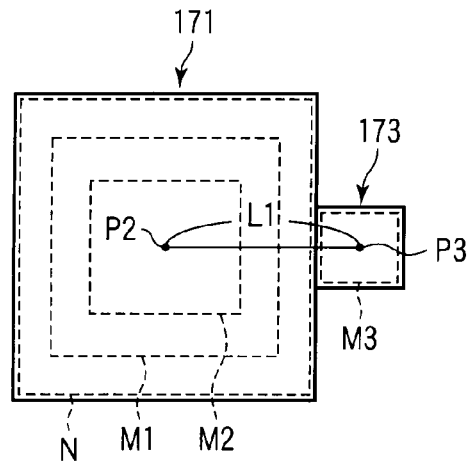
Sizes of field of views: N > M1 > M2 > M3
F I G. 11
FOV positions with detection surface being fixed
(FPD 171 and MA 173 are slid stepwise when FOV sizes N, M1, M2, and M3 are switched)
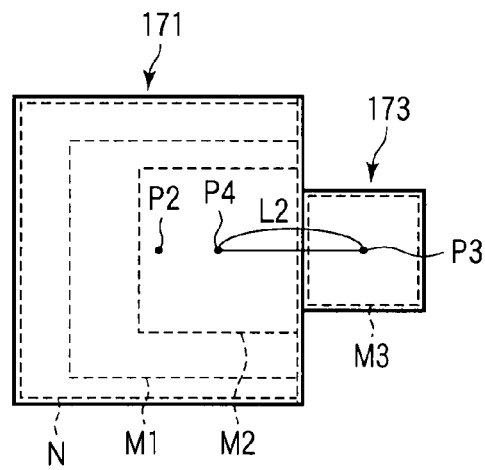
Sizes of field of views: N > M1 > M2 > M3
F I G. 12

X-RAY DIAGNOSTIC APPARATUS

CROSS-REFERENCE TO RELATED APPLICATIONS

This application is based upon and claims the benefit of priority from Japanese Patent Application No. 2009-244544, filed Oct. 23, 2009; the entire contents of which are incorporated herein by reference.

FIELD

Embodiments described herein relate generally to an X-ray diagnostic apparatus.

BACKGROUND

A flat panel detector (to be referred to as an FPD hereinafter) is used to perform X-ray fluoroscopy/radiography of blood vessels and organs. A micro angio detector (to be referred to as an MA hereinafter) has been devised for the extraction of fine portions (200 μm or less) such as perforating branches and asymmetric stents. An X-ray diagnostic apparatus has presently been developed, which includes both an FPD and an MA and can switch and use the FPD and MA.

The X-ray diagnostic apparatus capable of switching the FPD and the MA normally uses the FPD. This apparatus uses the MA to check a fine portion which cannot be checked with the FPD. The MA is placed in front of the FPD. An X-ray generating system is commonly used both when the FPD is used and when the MA is used. When switching the FPD and the MA, the operator needs to perform cumbersome operation of retracting and placing the FPD and the MA. In order to equalize the X-ray dose at the time of the use of the MA to the X-ray dose at the time of the use of the FPD, it is necessary to increase the size of the effective X-ray focal spot at the time of the use of the MA to that at the time of the use of the FPD. Increasing the size of the effective focal spot leads to a deterioration in image quality. That is, the guarantee of an X-ray dose has a trade-off relationship with a reduction in the size of an effective focal spot.

BRIEF DESCRIPTION OF THE DRAWINGS

FIG. 1 is a block diagram showing the arrangement of an X-ray diagnostic apparatus according to the first embodiment;

FIG. 5 is a block diagram showing the arrangement of an X-ray diagnostic apparatus according to the second embodiment;

FIG. 7 is a view showing a typical example of the location of an X-ray tube at the time of the use of an FPD in FIG. 5;

FIG. 9 is a view showing a typical example of a geometry at the time of normal fluoroscopy in FIG. 5;

FIG. 10 is a view showing a typical example of a geometry at the time of enlargement fluoroscopy/radiography in FIG. 5;

FIG. 11 is a view for explaining the first switching operation performed in response to an FOV size switching instruction under the control of a mechanism control unit in a modification; and FIG. 12 is a view for explaining the second switching operation performed in response to an FOV size switching instruction under the control of the mechanism control unit in the modification.

DETAILED DESCRIPTION

In general, according to one embodiment, an X-ray diagnostic apparatus includes an X-ray tube, first detector, second detector, arm, sliding mechanism, tilting mechanism, and control unit. The X-ray tube includes a cathode to emit electrons and an anode to generate X-rays upon receiving the electrons emitted from the cathode. The first detector detects the X-rays generated by the X-ray tube and has the first pixel size. The second detector detects the X-rays generated by the X-ray tube and has the second pixel size smaller than the first pixel size. The arm pivotally supports the X-ray tube, first detector, and second detector. The sliding mechanism is mounted on the arm. The sliding mechanism slidably supports the first and second detectors so as to irradiate one of the first and second detectors with the X-rays generated by the X-ray tube. The tilting mechanism is mounted on the arm. The tilting mechanism tiltably supports the X-ray tube to change the size of an effective X-ray focal spot on the anode. The control unit controls the sliding of the first and second detectors by the sliding mechanism upon interlocking with the tilting of the X-ray tube by the tilting mechanism.

The X-ray diagnostic apparatus according to this embodiment will be described below with reference to the views of the accompanying drawing.

First Embodiment

Figure 2:
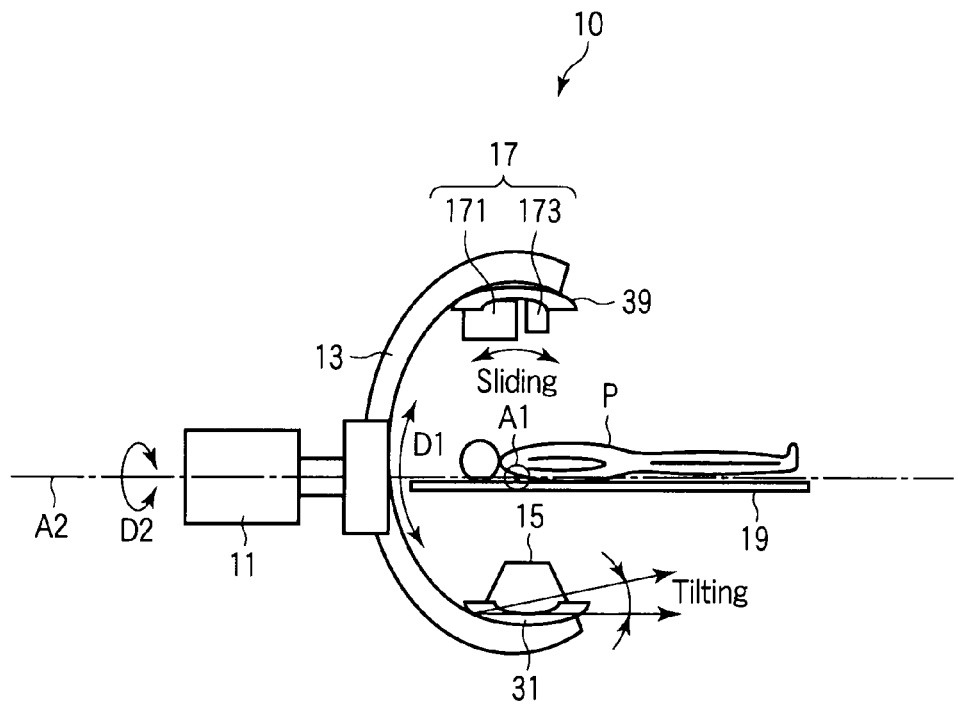
FIG. 2 is a schematic view showing an outer appearance of an imaging mechanism in FIG. 1.

FIG. 1 is a block diagram showing the arrangement of an X-ray diagnostic apparatus 1 according to the first embodiment. As shown in FIG. 1, the X-ray diagnostic apparatus 1 includes an imaging mechanism 10. FIG. 2 is a schematic view showing an outer appearance of the imaging mechanism 10. The imaging mechanism 10 includes a C-arm holder 11 swingably mounted or fixed on the floor with a stand (not shown). The C-arm holder 11 supports a C-arm 13 so as to allow it to slide around a rotation axis A1. The C-arm 13 slides around the rotation axis A1 so as to slide in a slide direction D1 along the C-shape of the C-arm 13. The C-arm holder 11 supports the C-arm 13 so as to allow it to rotate about a rotation axis A2 perpendicular to the rotation axis A1. The C-arm 13 rotates about the rotation axis A2 so as to rotate in a rotating direction D2. The intersection point between the rotation axis A1 and the rotation axis A2 is called an isocenter. The C-arm 13 operates around the rotation axis A1 and the rotation axis A2 to as to spatially fix the isocenter. An X-ray tube 15 and an X-ray detector 17 are mounted on the C-arm 13 so as to face each other.

When performing X-ray fluoroscopy/radiography, the operator moves a top 19 on which an object P is placed to a position between the X-ray tube 15 and the X-ray detector 17. The top 19 is supported by a bed (not shown) to be movable along the longitudinal direction, lateral direction, and vertical direction. The bed moves the top 19 in accordance with a driving signal from a bed driving unit 21.

The X-ray tube 15 generates X-rays upon receiving a high voltage and a filament current from a high voltage generating unit 25 under the control of an X-ray control unit 23. A collimator mechanism 27 is attached to the X-ray irradiation port of the X-ray tube 15. The collimator mechanism 27 is a so-called variable X-ray beam limiting device. That is, the collimator mechanism 27 movably supports the blades made of a material that blocks X-rays. The blades are formed from, for example, lead. Adjusting the positions of the blades will change the size and shape of a field of view (to be referred to as an FOV hereinafter). The collimator mechanism 27 moves the blades upon receiving a driving signal from a collimator mechanism driving unit 29.

The X-ray tube 15 is mounted on a tilting mechanism 31 mounted on the C-arm 13. The tilting mechanism 31 tiltably supports the X-ray tube 15. The tilting mechanism 31 is motor-driven to tilt the X-ray tube 15 upon receiving a driving signal from a tilting mechanism driving unit 33, thereby changing the size of an effective X-ray focal spot without greatly changing the X-ray dose. Note that an effective focal spot is an X-ray focal point viewed from the X-ray irradiation direction (e.g., in the direction in which the X-ray tube 15 is viewed from the X-ray detector 17). It is possible to independently drive the tilting mechanism 31 and the C-arm 13.

The X-ray detector 17 detects the X-rays generated by the X-ray tube 15. More specifically, the X-ray detector 17 includes an FPD 171 and an MA 173. The FPD 171 is an X-ray detector having a larger pixel size than the MA 173. The FPD 171 detects the X-rays generated by the X-ray tube 15 and generates the first image data corresponding to the detected X-rays. The pixel size of the generated first image corresponds to the pixel size of the FPD 171. The first image data is supplied to a first image input unit 35. The MA 173 is an X-ray detector having a smaller pixel size than the FPD 171. The MA 173 detects the X-rays generated by the X-ray tube 15 and generates the second image data corresponding to the detected X-rays. The pixel size of the generated second image corresponds to the pixel size of the MA 173. That is, the pixel size of the second image is smaller than the pixel size of the first image. The second image data is supplied to a second image input unit 37.

The FPD 171 and the MA 173 are arranged adjacent to each other on a sliding mechanism 39. The FPD 171 and the MA 173 may be arranged with or without a space between them. The C-arm 13 supports the FPD 171 and the MA 173 so as to allow them to slide along the arranging direction such that one of the FPD 171 and the MA 173 is included in an FOV. The arranging direction is parallel to, for example, the rotation axis A2. The sliding mechanism 39 is motor-driven to slide along the arranging direction (slide direction) upon receiving a driving signal from a sliding mechanism driving unit 41, thereby sliding the FPD 171 and the MA 173. Sliding the sliding mechanism 39 in this manner will switch the X-ray detector to be used from the FPD 171 to the MA 173 or from the MA 173 to the FPD 171. Note that it is possible to independently drive the sliding mechanism 39 and the C-arm 13.

The first image input unit 35 inputs the first image data from the FPD 171 to an image storage unit 43. The second image input unit 37 inputs the second image data from the MA 173 to the image storage unit 43.

An image processing unit 45 reads out and processes the first and second image data from the image storage unit 43 under the control of a system control unit 55. The image storage unit 43 stores the processed first and second image data.

The image storage unit 43 stores the first image data from the first image input unit 35, the second image data from the second image input unit 37, the processed first image data from the image processing unit 45, and the processed second image data from the image processing unit 45.

An image output unit 47 reads out the first and second image data from the image storage unit 43 under the control of the system control unit 55, and supplies the data to a display unit 49. The display unit 49 displays the first and second images from the image output unit 47 in a predetermined layout.

A mechanism control unit 51 controls the sliding mechanism driving unit 41, the bed driving unit 21, the collimator mechanism driving unit 29, and the tilting mechanism driving unit 33 under the control of the system control unit 55. More specifically, the mechanism control unit 51 controls the sliding mechanism driving unit 41 based on a control signal from the system control unit 55 to supply a driving signal to the sliding mechanism 39. The mechanism control unit 51 controls the bed driving unit 21 based on a control signal from the system control unit 55 to supply a driving signal to the bed. The mechanism control unit 51 controls the collimator mechanism driving unit 29 based on a control signal from the system control unit 55 to supply a driving signal to the collimator mechanism 27. The mechanism control unit 51 controls the tilting mechanism driving unit 33 based on a control signal from the system control unit 55 to supply a driving signal to the tilting mechanism 31.

An operation unit 53 accepts various kinds of commands and information inputs from the operator via an input device, and supplies operation signals corresponding to the accepted commands and information to the system control unit 55. As input devices, for example, a keyboard, a mouse, various kinds of buttons, a touch panel, and the like can be used. The input devices include a tilt button for the X-ray tube 15, a switching button for the FPD 171 and the MA 173, and a switching button for FOV sizes.

The system control unit 55 functions as the main component of the X-ray diagnostic apparatus 1. For example, the system control unit 55 controls the mechanism control unit 51, the X-ray control unit 23, the image processing unit 45, and the image output unit 47 in accordance with operation signals from the operation unit 53.

An example of the operation of the X-ray diagnostic apparatus 1 according to the first embodiment will be described in detail next. As described above, the X-ray diagnostic apparatus 1 according to the first embodiment is equipped with both the FPD 171 and the MA 173. The FPD 171 is used for normal X-ray fluoroscopy/radiography. The MA 173 is used for the observation of a fine portion (200 μm or less) such as perforating branches and asymmetric stents. The frequency in use of the FPD 171 is higher than that of the MA 173.

For example, the mechanism control unit 51 controls the sliding of the FPD 171 and MA 173 by the sliding mechanism driving unit 41 upon interlocking with the tilting of the X-ray tube 15 by the tilting mechanism 31. More specifically, as described above, the sliding mechanism driving unit 41 drives the sliding mechanism 39 under the control of the mechanism control unit 51 to slide the FPD 171 and the MA 173 so as to irradiate one of the FPD 171 and the MA 173 with the X-rays generated by the X-ray tube 15. The tilting mechanism driving unit 33 drives the tilting mechanism 31 under the control of the mechanism control unit 51 to tilt the X-ray tube so as to change the size of an effective focal spot. The mechanism control unit 51 controls the tilting mechanism 31 using the tilting mechanism driving unit 33 upon interlocking with the driving of the sliding mechanism 39 by the sliding mechanism driving unit 41.

For example, when the X-ray detector to be used is switched from the FPD 171 to the MA 173, the mechanism control unit 51 tilts the X-ray tube 15 to reduce the size of an effective focal spot. When the X-ray detector to be used is switched from the MA 173 to the FPD 171, the mechanism control unit 51 tilts the X-ray tube 15 to increase the size of the effective focal spot. As described above, the frequency in use of the FPD 171 is higher than that of the MA 173. Typically, for this reason, the mechanism control unit 51 tilts the X-ray tube 15 at the time of the use of the MA 173 relative to the tilt angle of the X-ray tube 15 at the time of the use of the FPD 171 as a reference angle.

Figure 3:
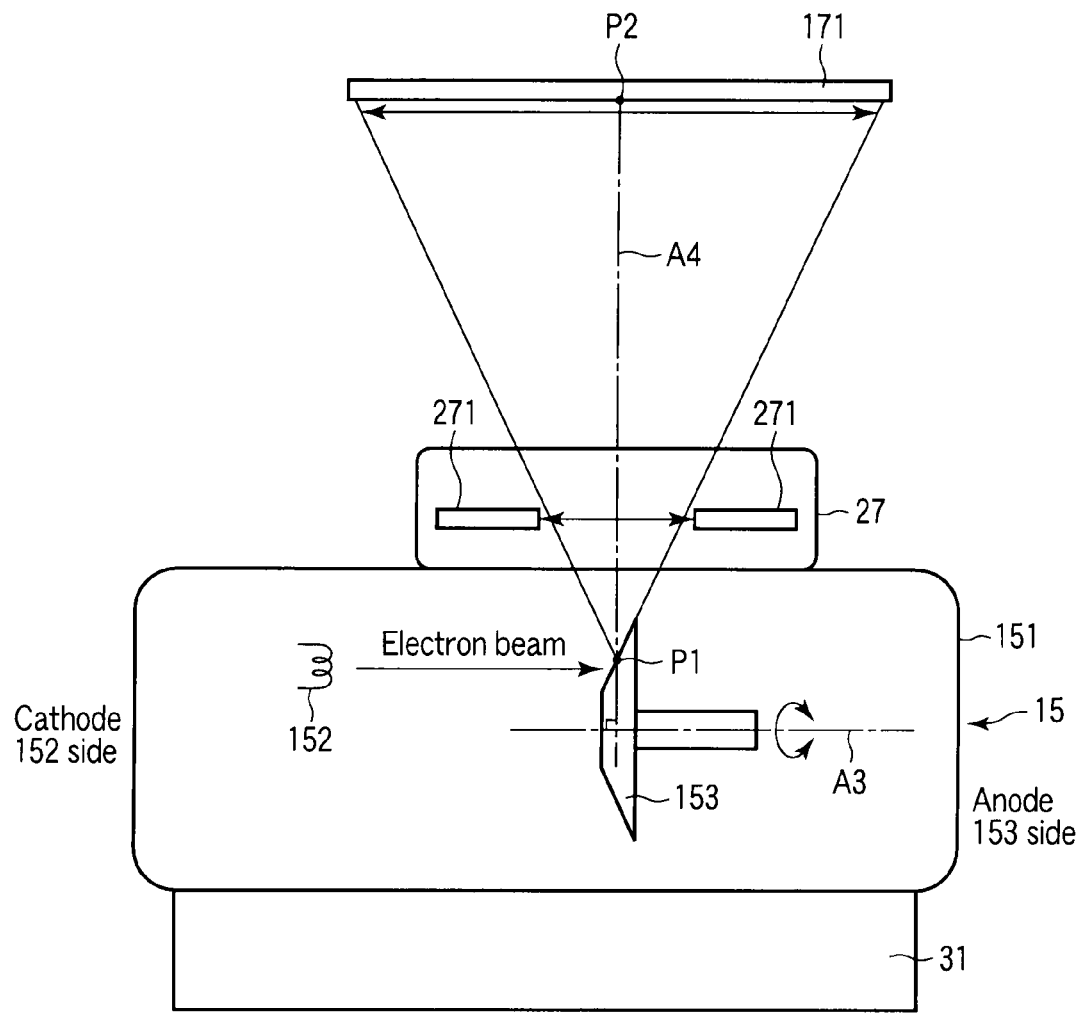
FIG. 3 is a view showing a typical example of the location of an X-ray tube at the time of the use of an FPD in FIG. 1.
Figure 4:
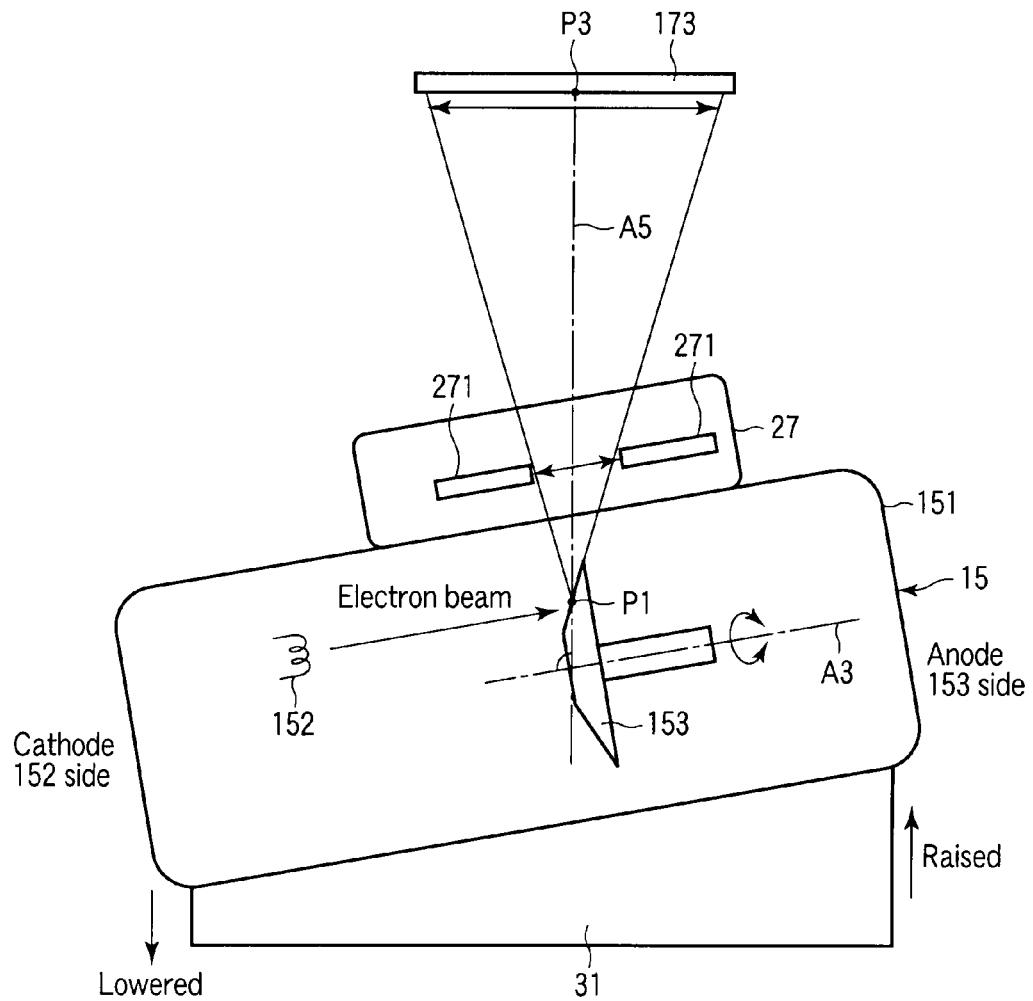
FIG. 4 is a view showing a typical example of the location of the X-ray tube at the time of the use of an MA in FIG. 1.

The structure of the X-ray tube 15 and the tilting of the X-ray tube 15 will be described in detail next with reference to FIGS. 3 and 4. FIG. 3 is a view showing the location of the X-ray tube 15 at the time of the use of the FPD 171. FIG. 4 is a view showing the location of the X-ray tube 15 at the time of the use of the MA 173.

As shown in FIGS. 3 and 4, the X-ray tube 15 includes a housing 151 whose interior is kept at a high vacuum. The housing 151 is provided with a cathode 152 and an anode 153. The cathode 152 is formed from a filament. The cathode 152 generates heat and electrons upon receiving a filament current from the high voltage generating unit 25. The anode 153 is a rotating anode which rotates about a rotation axis A3 at a high speed. The high voltage generating unit 25 applies a high voltage between the cathode 152 and the anode 153. The electrons generated by the cathode 152 by this high voltage are accelerated while being focused into a beam, and collide with the anode 153 during rotation. The anode 153 emits X-rays toward the X-ray irradiation port upon receiving electrons from the cathode 152. A region on the anode 153 with which electrons collide is called a focal point P1. Note that the focal point P1 viewed from the normal direction of the surface of the anode 153 is called an actual focal spot. A focal point P2 viewed from the X-ray irradiation direction (an axis A4 (to be referred to as an FPD-focal axis A4 hereinafter) connecting a detection surface center P2 of the FPD 171 to the focal point P1 in FIG. 3) is called an effective focal spot. The rotation axis A3 is parallel to the direction in which an electron beam travels straight from the cathode 152 to the anode 153. Note that the relative positional relationship between the cathode 152 and the anode 153 remains unchanged regardless of the tilt angle of the X-ray tube 15.

The X-ray irradiation port of the housing 151 is provided on the X-ray detector 17 side. The collimator mechanism 27 is attached to the X-ray irradiation port of the housing 151. Blades 271 for changing the FOV size are movably supported by the collimator mechanism 27. Typically, the collimator mechanism 27 is provided a plurality of blades 271. The collimator mechanism 27 can switch FOV sizes or form an X-ray irradiation field (FOV) into a rectangular or circular shape in accordance with the shape of the FPD 171 or MA 173 by placing the plurality of blades 271 at proper positions while interlocking them. The tilting mechanism 31 tiltably supports the opposite side of the housing 151 to the X-ray irradiation port.

As shown in FIG. 3, at the time of the use of the FPD 171, the tilting mechanism 31 supports the X-ray tube 15 so as to make the rotation axis A3 almost perpendicular to the FPD-focal axis A4. At the time of the use of the FPD 171, the tilt angle of the X-ray tube 15, i.e., the tilt angle of the rotation axis A3 relative to the FPD-focal axis A4, is set to nearly 90°, which is a reference angle.

As shown in FIG. 4, at the time of the use of the MA 173, the tilting mechanism 31 supports the X-ray tube 15 so as to make the rotation axis A3 tilt relative to an axis A5 (to be referred to as the MA-focal axis A5 hereinafter) connecting a detection surface center P3 of the MA 173 to the focal point P1. For example, the tilting mechanism 31 supports the X-ray tube 15 so as to make the anode 153 side of the housing 151 closer to the MA 173 than the cathode 152 side. At the time of the use of the MA 173, the tilt angle of the X-ray tube 15, i.e., the tilt angle of the rotation axis A3 relative to the MA-focal axis A5 viewed from the cathode 152 side, is set to an angle larger than 90°. Note that the detection surface center P3 of the MA 173 at the time of the use of the MA 173 is located on the FPD-focal axis A4 at the time of the use of the FPD 171. That is, the FPD-focal axis A4 at the time of the use of the FPD 171 overlaps the MA-focal axis A5 at the time of the use of the MA 173.

In addition, it is possible to keep the geometric enlargement ratio of the object P constant by making the detection surface center P2 at the time of the use of the FPD 171 coincide with the detection surface center P3 at the time of the use of the MA 173 and making the position of the focal point P1 stationary regardless of the tilt angle.

An example of the operation of tilting the X-ray tube 15, switching the X-ray detector 17, and moving the blades 271 under the control of the mechanism control unit 51 will be described next. For example, the mechanism control unit 51 tilts the X-ray tube 15, switches the X-ray detector 17, and moves the blades 271 in response to the pressing of the switching button for the X-ray detector 17 which is provided on the operation unit 53.

The mechanism control unit 51 stores the tilt angles of the X-ray tube 15 and the locations of the blades 271 for the use of the FPD 171 in the form of a table. Likewise, the mechanism control unit 51 stores the tilt angles of the X-ray tube 15 and the locations of the blades 271 for the use of the MA 173 in the form of a table. The tilt angle of the X-ray tube 15 and the locations of the blades 271 at the time of the use of the FPD 171 are set to make the FOV almost coincide with the shape and size of the detection surface of the FPD 171. The tilt angle of the X-ray tube 15 and the locations of the blades 271 at the time of the use of the MA 173 are set to make the FOV almost coincide with the shape and size of the detection surface of the MA 173. In this case, the tilt angle for the FPD 171 is set to 90°. The tilt angle for the MA 173 is set to an angle between 90° and 180° so as to make the size of the effective focal spot at the time of the use of the MA 173 become smaller than that at the time of the use of the FPD 171. More strictly, the tilt angle is set to an angle up to 90°+the target angle of the anode 153.

For example, upon receiving an instruction to switch from the FPD 171 to the MA 173, the mechanism control unit 51 reads out a tilt angle for the MA 173 from the table, and controls the tilting mechanism driving unit 33 to tilt the X-ray tube 15 at the readout tilt angle. The tilting mechanism driving unit 33 drives the tilting mechanism 31 to tilt the X-ray tube 15 to the tilt angle for the MA 173. Typically, the tilting mechanism 31 raises the anode 153 side of the housing 151 and lowers the cathode 152 side so as to set the X-ray tube 15 at the tilt angle for the MA 173. Likewise, upon receiving an instruction to switch from the FPD 171 to the MA 173, the mechanism control unit 51 reads out the locations of the blades 271 for the MA 173 and controls the tilting mechanism driving unit 33 to locate the blades 271 at the readout locations. The tilting mechanism driving unit 33 drives the collimator mechanism 27 to move the blades 271 to the locations for the MA 173.

Upon receiving an instruction to switch from the MA 173 to the FPD 171, the mechanism control unit 51 reads out the tilt angle for the FPD 171 from the table, and controls the tilting mechanism driving unit 33 to tilt the X-ray tube 15 at the readout tilt angle. The tilting mechanism driving unit 33 drives the tilting mechanism 31 to tilt the X-ray tube 15 to the tilt angle for the FPD 171. Typically, the tilting mechanism 31 lowers the anode 153 side of the housing 151 and raises the cathode 152 side to locate the X-ray tube 15 at the tilt angle for the FPD 171. Likewise, upon receiving an instruction to switch from the MA 173 to the FPD 171, the mechanism control unit 51 reads out the locations of the blades 271 for the FPD 171 from the table, and controls the tilting mechanism driving unit 33 to locate the blades 271 at the readout locations. The tilting mechanism driving unit 33 drives the collimator mechanism 27 to move the blades 271 to the locations for the MA 173.

As described above, the X-ray diagnostic apparatus 1 includes the sliding mechanism 39 for sliding the FPD 171 and the MA 173. The sliding mechanism 39 can quickly switch to the X-ray detector to be used by sliding the FPD 171 and the MA 173 by motor driving in response to a user's button operation. In the first embodiment, the sliding mechanism 39 eliminates the necessity to retract and place the FPD 171 and the MA 173 when switching them as in the prior art. The X-ray diagnostic apparatus can therefore reduce the labor of the user and the switching time associated with switching operation between the FPD 171 and the MA 173.

The X-ray diagnostic apparatus 1 includes the tilting mechanism 31 for tilting the X-ray tube 15. The tilting mechanism 31 can tilt the X-ray tube 15 to change the size of an effective focal spot in response to a user's button operation. More specifically, the tilting mechanism 31 tilts the rotation axis A3 (almost the same as the direction in which an electron beam travels straight) relative to the axes A4 and A5 connecting the detection surface center to the focal point. Changing the size of the effective focal spot by tilting the X-ray tube 15 can reduce the size of the effective focal spot while securing an X-ray dose at the time of the use of the MA 173. This can solve the conventional problem of the trade-off between the securement of an X-ray dose and the reduction in the size of the effective focal spot. This eliminates the necessity to increase the size of an effective focal point to secure an X-ray dose, and hence improves the sharpness of the second image originating from the MA 173 as compared with the prior art. It is therefore possible to accurately extract a fine portion while effectively using the characteristics of the MA 173.

The first embodiment can therefore provide an X-ray diagnostic apparatus which improves examination efficiency and examination accuracy.

According to the above description, this apparatus tilts the X-ray tube 15, switches the X-ray detector 17, and moves the blades 271 in response to an instruction to switch the X-ray detector 17. However, the first embodiment is not limited to this. For example, it is possible to tilt the X-ray tube 15, switch the X-ray detector 17, and move the blades 271 in response to an instruction to tilt the X-ray tube 15, an instruction to switch the sizes of an effective focal spot, or the like.

Second Embodiment

The second embodiment will be described below. Note that the same reference numerals as in the first embodiment denote constituent elements having almost the same functions, and a repetitive description will be made only when required.

Figure 6:
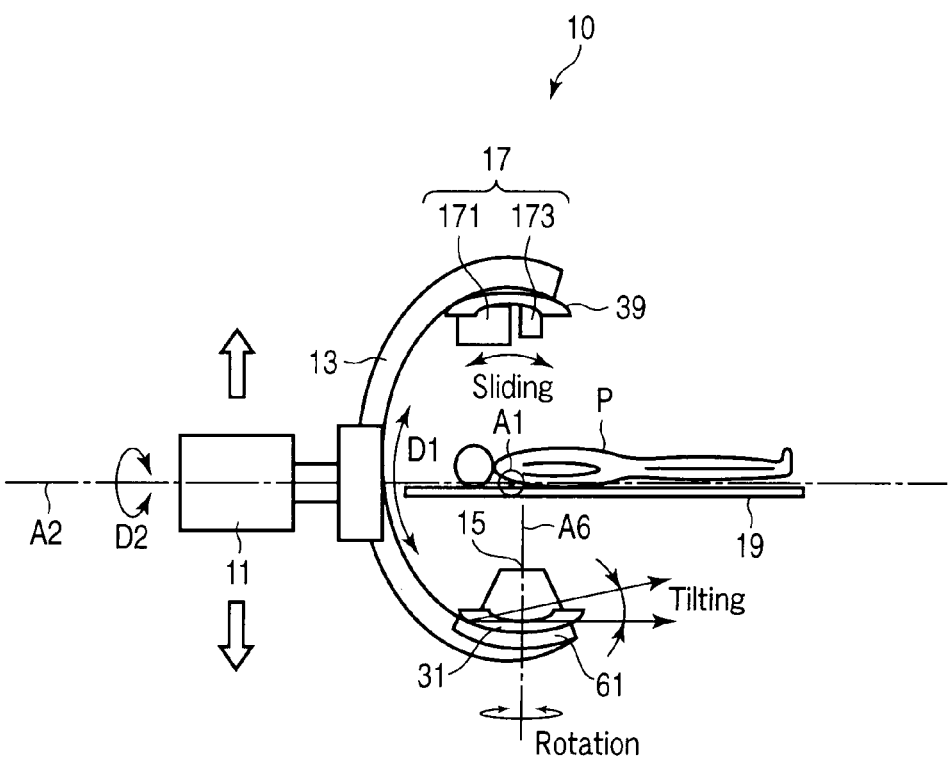
FIG. 6 is a schematic view showing an outer appearance of an imaging mechanism in FIG. 5.

FIG. 5 is a block diagram showing the arrangement of an X-ray diagnostic apparatus according to the second embodiment. FIG. 6 is a schematic view showing an outer appearance of an imaging mechanism 10 according to the second embodiment. As shown in FIGS. 5 and 6, the imaging mechanism 10 includes a rotating mechanism 61. The rotating mechanism 61 supports an X-ray tube 15 so as to allow it to rotate about a rotation axis A6. The rotating mechanism 61 is provided between, for example, a C-arm 13 and the X-ray tube 15. The rotation axis A6 is defined by an axis connecting the detection surface center of an X-ray detector 17 in use to an effective focal spot. That is, when the X-ray detector 17 in use is an FPD 171, the rotation axis A6 is defined by an FPD-focal axis A4. When the X-ray detector 17 in use is the MA 173, the rotation axis A6 is defined by an MA-focal axis A5. The rotating mechanism 61 rotates about the rotation axis A6 upon receiving a driving signal from a rotating mechanism driving unit 63.

The imaging mechanism 10 also includes a vertical moving mechanism 65. The vertical moving mechanism 65 supports the C-arm 13 so as to allow it to move along an almost vertical direction. The vertical moving mechanism 65 vertically moves the C-arm 13 in an almost vertical direction upon receiving a driving signal from a vertical moving mechanism driving unit 67. A mechanism control unit 51 controls the rotating mechanism driving unit 63 and the vertical moving mechanism driving unit 67 under the control of a system control unit 55. More specifically, the mechanism control unit 51 controls the rotating mechanism driving unit 63, based on a control signal from the system control unit 55, to supply a driving signal to the rotating mechanism 61. The mechanism control unit 51 controls the vertical moving mechanism driving unit 67, based on a control signal from the system control unit 55, to supply a driving signal to the vertical moving mechanism 65.

Tilting and rotation of the X-ray tube 15 will be described next.

First of all, a restriction on a change in the size of an effective focal spot which is made by tilting the X-ray tube 15 will be described first. When a tilting mechanism 31 tilts the X-ray tube 15, the size of the effective focal spot changes only along an axis perpendicular to an axis connecting the X-ray focal point to the detection surface center. Tilting the X-ray tube 15 can improve only the spatial resolution of an X-ray image (first or second image) in the X or Y direction.

The mechanism control unit 51 according to the second embodiment can rotate the X-ray tube 15. Therefore, tilting and rotating the X-ray tube 15 can improve the spatial resolution of an X-ray image in an arbitrary direction.

Figure 8:
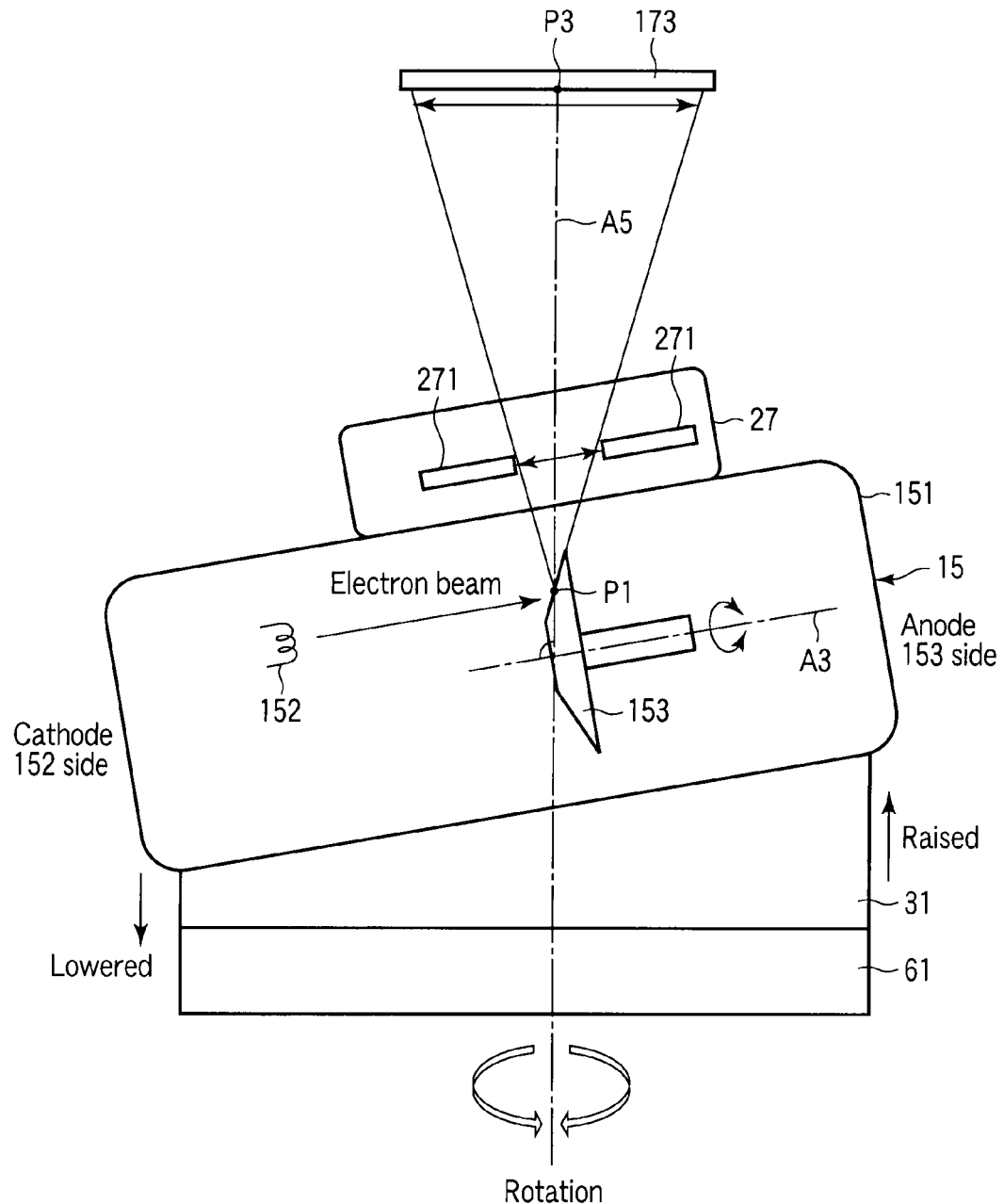
FIG. 8 is a view showing a typical example of the location of the X-ray tube at the time of the use of an MA in FIG. 5.

Tilting and rotation of the X-ray tube 15 will be described in detail next with reference to FIGS. 7 and 8. FIG. 7 is a view showing a typical example of the location of the X-ray tube 15 at the time of the use of the FPD 171. FIG. 8 is a view showing a typical example of the location of the X-ray tube 15 at the time of the use of the MA 173.

As shown in FIG. 7, at the time of the use of the FPD 171, the tilting mechanism 31 supports the X-ray tube 15 so as to make a rotation axis A3 almost perpendicular to the FPD-focal axis A4. At the time of the use of the FPD 171, the rotating mechanism 61 supports the X-ray tube 15 so as to set the rotational angle of the X-ray tube 15 to a reference rotational angle. The rotational angle of the X-ray tube 15 is the angle around the FPD-focal axis A4. The rotational angle of the X-ray tube 15 is set to, for example, an angle between −90° and +90°. The reference rotational angle is 0°.

As shown in FIG. 8, at the time of the use of the MA 173, the tilting mechanism 31 supports the X-ray tube 15 so as to tilt the rotation axis A3 relative to the MA-focal axis A5. At the time of the use of the MA 173, the rotating mechanism 61 supports the X-ray tube 15 so as to make the rotational angle of the X-ray tube 15 deviate from the reference rotational angle. Typically, the X-ray tube 15 is placed at a rotational angle complying with an instruction issued by the user via an operation unit 53.

Note that the rotational angle of the X-ray tube 15 may differ from the reference rotational angle even at the time of the use of the FPD 171. In addition, even at the time of the use of the MA 173, the rotational angle of the X-ray tube 15 may coincide with the reference rotational angle.

Control of sliding of the FPD 171 and MA 173, tilting of the X-ray tube 15, and rotation of the X-ray tube 15 which are performed under the control of the mechanism control unit 51 will be described next. For example, the mechanism control unit 51 tilts the X-ray tube 15, switches the X-ray detector 17, and moves the blades 271 in response to the pressing of the switching button of the X-ray detector 17, which is provided on the operation unit 53, by the user.

After executing these operations, the mechanism control unit 51 rotates the X-ray tube 15 in response to the pressing of the rotation button of the X-ray tube 15 by the user. For example, while the operator presses the rotation button of the X-ray tube 15, the X-ray tube 15 rotates at a predetermined rotational speed. When the operator releases the rotation button, the X-ray tube 15 stops. This makes it possible to change the size of an effective focal spot along an arbitrary direction, thereby improving the spatial resolution of an X-ray image along an arbitrary direction. The operation of changing the size of an effective focal spot by rotating the X-ray tube 15 is clinically effective especially when a high spatial resolution required by the MA 173 is required.

According to the above description, the rotating mechanism 61 is provided between the C-arm 13 and the X-ray tube 15. However, the second embodiment is not limited to this. For example, the rotating mechanism 61 may be implemented by the rotation of the C-arm suspended from the ceiling or the rotation of the C-arm upon floor rotation.

It is possible to rotate the X-ray detector 17 upon interlocking with the rotation of the X-ray tube 15, as needed. In this case, the rotation axis of the X-ray detector 17 coincides with the rotation axis of the X-ray tube 15 (i.e., the FPD-focal axis A4 or the MA-focal axis A5).

A collimator mechanism 27 may be or may not be fixed to the X-ray tube 15. When the collimator mechanism 27 is fixed to the X-ray tube 15, the collimator mechanism 27 rotates together with the X-ray tube 15. When the collimator mechanism 27 is not fixed to the X-ray tube 15, the collimator mechanism 27 does not rotate together with the X-ray tube 15. In this case, a rotating unit (not shown) may rotate the collimator mechanism 27 independently of the X-ray tube 15.

The vertical movement of the C-arm 13 will be described in detail next with reference to FIGS. 9 and 10. FIG. 9 is a view showing a typical example of a geometrical arrangement at the time of normal fluoroscopy/radiography. FIG. 10 is a view showing a typical example of a geometrical arrangement at the time of enlargement fluoroscopy/radiography. Assume that in FIGS. 9 and 10, the X-ray detector 17 to be used is the MA 173. However, the second embodiment is not limited to this, and the X-ray detector 17 to be used may be the FPD 171. In addition, it is possible to use the FPD 171 at the time of normal fluoroscopy/radiography and use the MA 173 at the time of enlargement fluoroscopy/radiography. In this case, as described above, a sliding mechanism 39 slides the FPD 171 and the MA 173 to switch them.

As shown in FIG. 9, when performing fluoroscopy/radiography at a normal geometric enlargement ratio, the operator sets the height of the C-arm 13 so as to locate the imaging area at almost the midpoint between the MA 173 and the X-ray tube 15. Typically, the imaging area is defined by a partial region of an object within an X-ray beam. As shown in FIG. 10, when performing fluoroscopy/radiography at a geometric enlargement ratio higher than the normal ratio, the operator sets the height of the C-arm 13 so as to locate the imaging area closer to the X-ray tube 15 than when performing normal fluoroscopy/radiography. Note that the second embodiment can also be applied to a case in which fluoroscopy/radiography is performed at an enlargement ratio lower than the normal ratio. In this case, the operator sets the height of the C-arm 13 so as to locate the imaging area farther from the X-ray tube 15 than when performing normal fluoroscopy/radiography.

The mechanism control unit 51 vertically moves the C-arm 13 in response to the pressing of the enlargement button for the C-arm 13, which is provided on the operation unit 53, by the user. For example, while the operator presses the vertical movement button, the C-arm 13 moves up or down toward the X-ray tube 15 at a predetermined velocity along the vertical direction. For example, as shown in FIGS. 9 and 10, when the X-ray tube 15 is positioned below the top 19, the C-arm 13 moves up to increase the enlargement ratio. In contrast, when the X-ray tube 15 is positioned above the top 19, the C-arm 13 moves down to increase the enlargement ratio.

The operation of adjusting the height of the C-arm 13 is not limited to manual operation by the user. The mechanism control unit 51 may switch to one of a plurality of preset enlargement ratios which is designated by the user. In this case, the mechanism control unit 51 may store a table which associates a plurality of enlargement ratios with a plurality of locations of the C-arm 13. When the user designates an enlargement ratio, the mechanism control unit 51 specifies the location of the C-arm 13 which is associated with the designated enlargement ratio on the table. The mechanism control unit 51 then controls the vertical moving mechanism driving unit 67 in accordance with the specified location. The vertical moving mechanism driving unit 67 moves the C-arm 13 to the specified location.

By changing the height of the C-arm 13 in this manner, the mechanism control unit 51 can increase the geometric image enlargement ratio without degrading the resolution of the X-ray detector 17.

Note that the method of changing a geometric image enlargement ratio is not limited to the operation of vertically moving the C-arm 13. The mechanism control unit 51 may change the geometric image enlargement ratio by vertically moving a top 19. When vertically moving the top 19, the mechanism control unit 51 can change the geometric image enlargement ratio by the same operation as that performed when vertically moving the C-arm 13. When, for example, performing fluoroscopy/radiography at the normal enlargement ratio, the operator sets the height of the top 19 so as to locate the imaging area at almost the midpoint between the MA 173 and the X-ray tube 15. When performing fluoroscopy/radiography at a geometric enlargement ratio higher than the normal ratio, the operator sets the height of the top 19 so as to locate the imaging area closer to the X-ray tube 15 than when performing normal fluoroscopy/radiography. When performing fluoroscopy/radiography at a geometric enlargement ratio lower than the normal ratio, the operator sets the height of the top 19 so as to locate the imaging area farther from the X-ray tube 15 than when performing normal fluoroscopy/radiography.

The second embodiment can therefore provide an X-ray diagnostic apparatus which improves examination efficiency and examination accuracy.

(Modification)

When performing X-ray fluoroscopy/radiography, the operator may switch FOV sizes. An X-ray diagnostic apparatus according to this modification performs the operation of tilting the X-ray tube 15, switching the X-ray detector 17, and moving the blades 271 upon interlocking with the switching of FOV sizes. The X-ray diagnostic apparatus according to the modification will be described below. Note that the same reference numerals as in the first embodiment denote constituent elements having almost the same functions, and a repetitive description will be made only when required.

The mechanism control unit 51 tilts the X-ray tube 15, switches the X-ray detector 17, and moves the blades 271 in response to the switching of FOV sizes via the operation unit 53. Typically, a plurality of FOV sizes are prepared. The mechanism control unit 51 stores a table which associates the respective FOV sizes with the tilt angles of the X-ray tube 15, the types of X-ray detectors 17, and the locations of the blades 271. For the sake of concreteness, assume that four FOV sizes are prepared, namely FOV sizes N, M1, M2, and M3 in descending order. The FOV sizes N, M1, and M2 are used at the time of the use of the FPD 171. The size M3 is used at the time of the use of the MA 173. The FOV size N is the standard size at the time of the use of the FPD 171.

There are two types of X-ray detector switching operations according to this modification. The first switching operation is a method of sliding the FPD 171 and the MA 173 only when switching between the FOV sizes M2 and M3. The second switching operation is a method of sliding the FPD 171 and the MA 173 stepwise whenever all the FOV sizes N, M1, M2, and M3 are switched.

The first switching operation will be described first.

FIG. 11 is a view for explaining the first switching operation performed for the X-ray detector 17 in response to an FOV size switching instruction. FIG. 11 shows the FOV positions viewed from the detection surface (the FOV positions with the detection surface being fixed). The centers of the FOVs having the FOV sizes N, M1, and M2 on the detection surface of the FPD 171 coincide with the detection surface center P2 of the FPD 171 and remain stationary. The center of the FOV having the FOV size M3 on the detection surface of the MA 173 coincides with the detection surface center P3 of the MA 173. Referring to FIG. 11, it looks as if the FOV center were moving during switching between the sizes M2 and M3. In practice, however, the FOV center remains stationary, and the FPD 171 and the MA 173 slide.

As shown in FIG. 11, when the operator issues an instruction to switch between the FOV sizes N, M1, and M2 via the operation unit 53, the sliding mechanism control unit 51 makes the sliding mechanism driving unit 41 stand by for sliding operation. When the operator issues an instruction to switch between the FOV sizes M2 and M3 via the operation unit 53, the sliding mechanism control unit 51 causes the sliding mechanism driving unit 41 to perform sliding operation. In this case, the sliding mechanism driving unit 41 slides the sliding mechanism 39 to switch between the FPD 171 and the MA 173. More specifically, when the operator issues an instruction to switch from the FOV size M2 to the FOV size M3, the sliding mechanism driving unit 41 drives the sliding mechanism 39 to slide the FPD 171 and the MA 173 so as to make the detection surface of the FPD 171 fall outside the FOV and make the detection surface of the MA 173 fall within the FOV. In this case, the sliding mechanism 39 slides the FPD 171 and the MA 173 by a distance L1 between the detection surface center P2 of the FPD 171 and the detection surface center P3 of the MA 173.

As described above, the first switching operation makes it possible to automatically switch the X-ray detector to be used from the FPD 171 to the MA 173 in response to an instruction to switch to the FOV size for the MA 173. As is obvious from a comparison with the second switching operation (to be described later), it is possible to make the centers of the FOVs of all the FOV sizes coincide with the detection surface center.

The second switching operation will be described next.

FIG. 12 is a view for explaining the second switching operation for the X-ray detector 17 which is performed in response to an instruction to switch FOV sizes. Like FIG. 11, FIG. 12 shows the FOV positions viewed from the detection surface (the FOV positions with the detection surface being fixed). The center positions of the FOVs having the FOV sizes N, M1, and M2 on the detection surface of the FPD 171 change. More specifically, in order to minimize the slide amount at the time of X-ray detector switching, the FOV position is shifted to the MA 173 side as the FOV size decreases. Referring to FIG. 12, it looks as if the FOV center were moving every time FOV sizes are switched. In practice, however, the FOV center remains stationary, and the FPD 171 and the MA 173 slide stepwise.

For the second switching operation, the mechanism control unit 51 stores a table which associates, for example, FOV sizes with the locations of the X-ray detector 17 (the FPD 171 and the MA 173). In order to minimize the slide amount at the time of X-ray detector switching, the locations of the FPD 171 and MA 173 are set to make one side of the FOV coincide with the boundary between the detection surface of the FPD 171 and the detection surface of the MA 173.

When the operator issues an instruction to switch between the FOV sizes N, M1, and M2 via the operation unit 53, the mechanism control unit 51 performs the first sliding operation. In the first sliding operation, the mechanism control unit 51 reads out, from the table, the locations of the FPD 171 and MA 173 which are associated with the FOV size after switching, and controls the sliding mechanism driving unit 41 to locate the FPD 171 and the MA 173 at the readout locations. The sliding mechanism driving unit 41 drives the sliding mechanism 39 to slide the FPD 171 and the MA 173 to the readout locations. When the operator issues an instruction to switch between the FOV sizes M2 and M3 via the operation unit 53, the mechanism control unit 51 performs the second sliding operation. In the second sliding operation, the mechanism control unit 51 reads out, from the table, the locations of the FPD 171 and MA 173 which are associated with the FOV size after switching, and controls the sliding mechanism driving unit 41 to locate the FPD 171 and the MA 173 at the readout locations. The sliding mechanism driving unit 41 drives the sliding mechanism 39 to slide the FPD 171 and the MA 173 to the readout locations. When the operator issues an instruction to switch from the FOV size M2 to the FOV size M3, the sliding mechanism 39 slides the FPD 171 and the MA 173 by a distance L2 between a center P4 of the FOV having the size M2 and the detection surface center P3 of the MA 173.

As described above, like the first switching operation, the second switching operation allows to automatically switch the X-ray detector to be used from the FPD 171 to the MA 173 in response to an instruction to switch to the FOV size for the MA 173. In this case, the slide amount L2 is smaller than the slide amount L1 in the first switching operation. As compared with the first switching operation, therefore, the second switching operation allows to decrease the slide amount at the time of X-ray detector switching by the difference between the distance L1 and the distance L2, thereby implementing smooth switching operation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an X-ray tube including a cathode to emit electrons and an anode to generate X-rays upon receiving electrons emitted from the cathode;
a first detector configured to detect X-rays generated by the X-ray tube and having a first pixel size;
a second detector configured to detect X-rays generated by the X-ray tube and having a second pixel size smaller than the first pixel size;
an arm configured to pivotally support the X-ray tube, the first detector, and the second detector;
a sliding mechanism mounted on the arm and configured to slide the first detector and the second detector so as to irradiate only one of the first detector and the second detector with X-rays generated by the X-ray tube;
a tilting mechanism mounted on the arm and configured to tiltably support the X-ray tube so as to change a size of an effective X-ray focal spot on the anode; and
a control unit configured to perform interlocking control of sliding of the first detector and the second detector by the sliding mechanism and tilting of the X-ray tube by the tilting mechanism.

2. The apparatus according to claim 1, further comprising:
a sliding mechanism driving unit configured to drive the sliding mechanism to slide the first detector and the second detector so as to irradiate one of the first detector and the second detector with X-rays generated by the X-ray tube, and
a tilting mechanism driving unit configured to drive the tilting mechanism and tilt the X-ray tube to change the size of the effective X-ray focal spot on the anode, wherein
the control unit controls the tilting mechanism by the tilting mechanism driving unit upon interlocking with driving of the sliding mechanism by the sliding mechanism driving unit.

3. The apparatus according to claim 1, wherein the tilting mechanism supports the X-ray tube so as to allow a rotation axis of the anode to tilt relative to an axis connecting one of a detection surface center of the first detector and a detection surface center of the second detector to the effective focal spot.

4. The apparatus according to claim 1, further comprising a tilting mechanism driving unit configured to drive the tilting mechanism in accordance with an instruction from a user.

5. The apparatus according to claim 1, further comprising a sliding mechanism driving unit configured to drive the sliding mechanism in accordance with an instruction from a user.

6. The apparatus according to claim 1, further comprising:
a collimator mechanism attached to the X-ray tube and configured to movably support an X-ray shielding member to change a size of a field of view, and
a collimator mechanism driving unit configured to drive the collimator mechanism in accordance with an instruction from a user.

7. The apparatus according to claim 1, further comprising:
a collimator mechanism attached to the X-ray tube and configured to movably support an X-ray shielding member to change a size of a solid angle of X-rays reaching one of the first detector and the second detector,
a collimator driving unit configured to drive the collimator mechanism to change a size of a field of view stepwise in accordance with an instruction from a user, and
a sliding mechanism driving unit configured to drive the sliding mechanism so as to slide the first detector and the second detector stepwise every time the collimator driving unit changes the size of the field of view.

8. The apparatus according to claim 1, further comprising a rotating mechanism configured to rotatably support the X-ray tube, wherein
the control unit controls sliding of the first detector and the second detector by the sliding mechanism, tilting of the X-ray tube by the tilting mechanism, and rotation of the X-ray tube by the rotating mechanism.

9. The apparatus according to claim 8, wherein the rotating mechanism supports the X-ray tube so as to allow the X-ray tube to rotate about an axis connecting one of a detection surface center of the first detector and a detection surface center of the second detector to the effective focal spot.

10. The apparatus according to claim 9, further comprising a rotating mechanism driving unit configured to drive the rotating mechanism in accordance with an instruction from a user.

11. The apparatus according to claim 1, further comprising:
a vertical moving mechanism configured to support the arm so as to allow the arm to vertically move, and
a vertical moving mechanism driving unit configured to drive the vertical moving mechanism to change a geometric image enlargement ratio.

12. The apparatus according to claim 1, further comprising:
a vertical moving mechanism configured to support a top on which an object is placed so as to allow the top to vertically move, and
a vertical moving mechanism driving unit configured to drive the vertical moving mechanism to change a geometric image enlargement ratio.

* * * * *